(12) United States Patent  (10) Patent No.: US 8,657,834 B2
Burgi  (45) Date of Patent: Feb. 25, 2014

(54) DOUBLE OFFSET SURGICAL TOOL HANDLE ASSEMBLY HAVING A LOCKING LINKAGE ALIGNED ALONG TWO DIFFERENT PLANES

(75) Inventor: Jonas Burgi, Moutier (CH)

(73) Assignee: Greatbatch Medical S.A., Orvin (CH)

( * ) Notice: Subject to any disclaimer, the term of this patent is extended or adjusted under 35 U.S.C. 154(b) by 254 days.

(21) Appl. No.: 13/040,309

(22) Filed: Mar. 4, 2011

(65) Prior Publication Data

US 2012/0071862 A1  Mar. 22, 2012

Related U.S. Application Data

(60) Provisional application No. 61/310,741, filed on Mar. 5, 2010.

(51) Int. Cl.
 *A61B 17/58* (2006.01)
 *A61B 17/60* (2006.01)
 *A61F 2/00* (2006.01)

(52) U.S. Cl.
 USPC .......................................................... 606/99

(58) Field of Classification Search
 USPC ............. 606/79–85, 86 A, 86 B, 99, 280–299
 See application file for complete search history.

(56) References Cited

U.S. PATENT DOCUMENTS

| | | |
|---|---|---|
| D272,648 S | 2/1984 | Bolesky et al. |
| D273,806 S | 5/1984 | Bolesky et al. |
| 4,765,328 A | 8/1988 | Keller et al. |
| 4,921,493 A | 5/1990 | Webb, Jr. et al. |
| 5,089,003 A | 2/1992 | Fallin et al. |
| 5,124,106 A | 6/1992 | Morr et al. |
| 5,234,432 A | 8/1993 | Brown |
| 5,261,915 A | 11/1993 | Durlacher et al. |
| 5,324,293 A | 6/1994 | Rehmann |
| 5,342,362 A | 8/1994 | Kenyon et al. |
| 5,454,815 A | 10/1995 | Geisser et al. |
| 5,665,091 A | 9/1997 | Noble et al. |
| 5,707,374 A | 1/1998 | Schmidt |
| 5,993,455 A | 11/1999 | Noble |
| 6,120,508 A | 9/2000 | Grunig et al. |

(Continued)

FOREIGN PATENT DOCUMENTS

| | | |
|---|---|---|
| DE | 202008017199 | 3/2009 |
| EP | 0938869 | 9/1999 |
| FR | 2847453 | 5/2004 |
| WO | 2006061708 | 6/2006 |

OTHER PUBLICATIONS

European Search Report dated Jun. 29, 2011.

*Primary Examiner* — Andrew Yang
*Assistant Examiner* — Diana S Jones
(74) *Attorney, Agent, or Firm* — Michael F. Scalise

(57) ABSTRACT

A surgical tool handle for releasable connection to a surgical tool is described. The tool handle comprises a housing providing a linkage chamber extending from a proximal housing grip end to a distal housing tool end for receiving a surgical tool. A tool linkage is partially housed within the housing linkage chamber comprising an axial handle region extending along axis A-A and a radiused housing region curving about a focal point. That way, a locking pawl of the tool linkage changes planes from its proximal end to a distal extending hook end. This provides a relatively short connection to a surgical tool that is optimum in the tight space requirements of a minimally invasive hip surgery.

19 Claims, 6 Drawing Sheets

(56) References Cited

U.S. PATENT DOCUMENTS

| | | |
|---|---|---|
| 6,663,636 B1 | 12/2003 | Lin |
| 2005/0171548 A1 | 8/2005 | Kelman |
| 2007/0167952 A1* | 7/2007 | Burgi et al. .................. 606/99 |
| 2008/0004628 A1 | 1/2008 | White |
| 2008/0033444 A1 | 2/2008 | Bastian et al. |
| 2008/0255565 A1* | 10/2008 | Fletcher ..................... 606/80 |

* cited by examiner

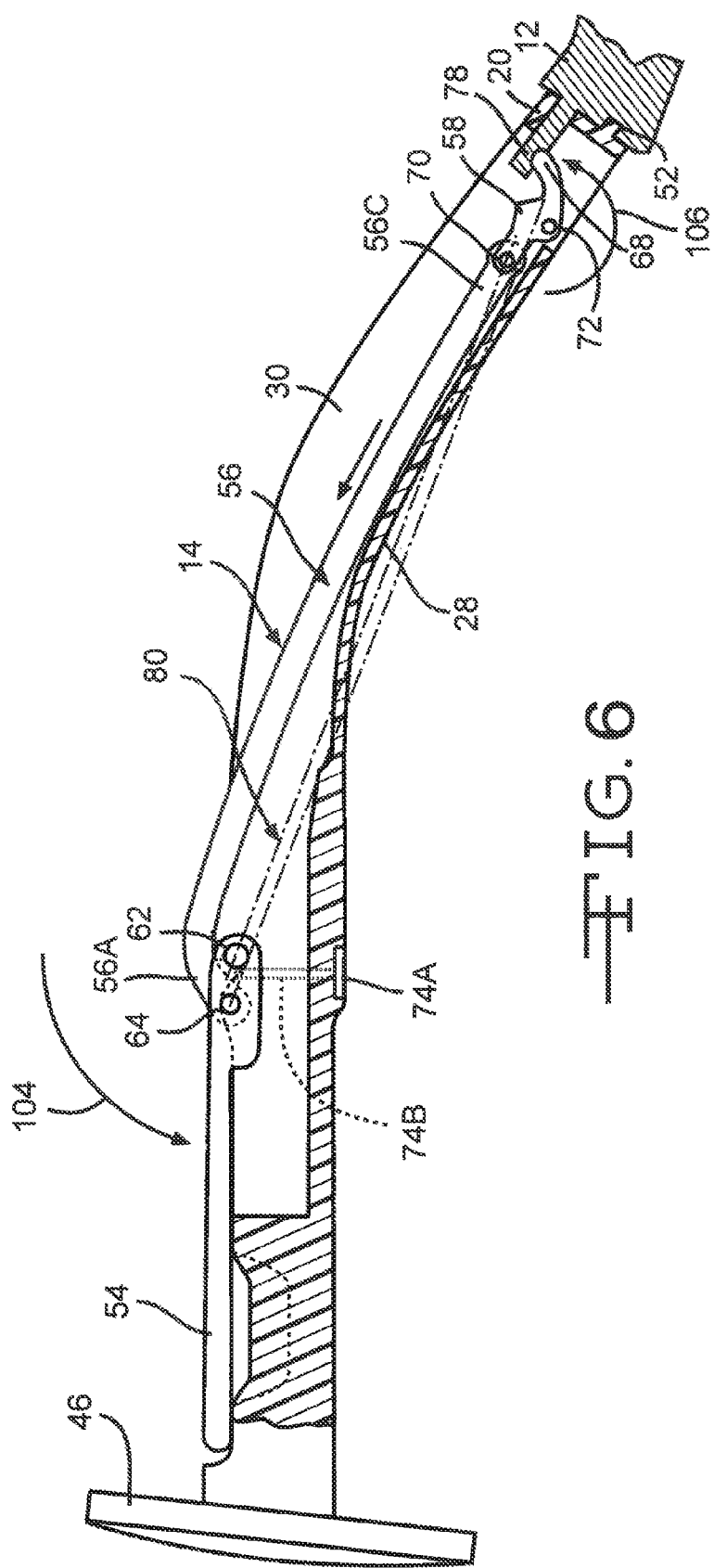

DOUBLE OFFSET SURGICAL TOOL HANDLE ASSEMBLY HAVING A LOCKING LINKAGE ALIGNED ALONG TWO DIFFERENT PLANES

CROSS REFERENCE TO RELATED APPLICATION

This application claims priority to U.S. provisional application Ser. No. 61/310,741, filed on Mar. 5, 2010.

FIELD OF THE INVENTION

This invention relates to surgical tools for aiding in the installation of orthopedic prostheses in patients. More particularly, the present invention relates to an easily sterilizable handle assembly for use with a surgical tool in preparing a bone site, and for use in installing a prosthesis in the bone.

BACKGROUND OF THE INVENTION

Complicated surgical tool handles typically have crevices and recesses that are difficult to clean with relative ease without disassembly into separate component parts. Tool handles that are not properly cleaned and sterilized increase the risk of disease transfer from patient to patient. This is especially true following the emergence of certain "prions" that are not killed by normal hospital sterilization. A prion is a type of infectious agent made only of protein.

Further, in surgical procedures in which access to the treatment site is limited, it is difficult to use current solutions without subjecting the patient to repeated abrasion and tissue trauma when inserting and extracting surgical instruments.

Additionally, the insertion of a prosthetic implant is often problematic, and the orientation of the implant in a properly prepared recess is often critical to minimize recovery time of the patient. Still further, once the appropriate position of the tool is selected, it is often difficult to ensure that the position does not change upon insertion of the assembly through the incision.

It would be beneficial, therefore, to have an orthopedic tool handle that easily connects to a surgical tool, and that is readily adjustable, disassemblable, and cleanable. Additionally, it would be beneficial if the tool were partially disassembled for cleaning without the need to completely separate the component parts of the handle from each other. Further, it would be beneficial to have a handle that enables the surgeon to better maneuver and position a tool head to facilitate preparing a bone site to receive a prosthetic implant in a particular angular orientation.

SUMMARY OF THE INVENTION

A surgical tool handle aids a surgeon in controlling the use of a tool during surgery, for example, during preparation of a femoral cavity for reception of hip joint prosthesis. The present invention is such a surgical tool handle, but adapted to facilitate sterilization. That way, the present tool handle allows for partial disassembly to facilitate sterilization, while remaining loosely intact to prevent the separation of component parts from the device as a whole.

The present surgical handle comprises a housing providing a linkage chamber housing a tool linkage. The housing extends from a proximal housing grip end to a distal housing tool end for receiving a tool. The tool linkage comprising: a handle lever attached to the housing by a proximal housing pivot pin to thereby provide a first pivotable connection between the tool linkage and the housing; a locking pawl attached to the housing by a distal housing pivot pin to thereby provide a second pivotable connection between the tool linkage and the housing; an inverted linkage comprising a proximal inverted linkage end and a distal inverted linkage end connected by a first free pivot pin to the handle lever to thereby provide a third pivotable connection; and a main linkage comprising a proximal main linkage end connected by a second free pivot pin to the proximal inverted linkage end adjacent to the proximal housing end in a fourth pivotable connection and a distal main linkage end connected by a third free pivot pin to the locking pawl adjacent to the distal housing end in a fifth pivotable connection.

During use, the handle lever is pivotable about the proximal housing pivot pin from a first, opened position spaced a maximum distance along a range of motion from the proximal housing end to a second, closed position spaced at a closer distance along the range of motion relative to the proximal housing end than the first position. This movement causes the inverted linkage, connected to the handle lever by the first free pivot pin, to move in a proximal direction to thereby move the main linkage, connected to the inverted linkage at the second free pivot pin, in a proximal direction toward the proximal housing end. This causes the locking pawl, connected to the distal main linkage end by the third free pivot pin, to pivot with respect to the housing on the distal housing pivot pin from an open configuration ready to receive a surgical tool for attachment to the housing to a closed configuration engageable with a surgical tool supported at the distal housing tool end.

In that respect, the present handle assembly is an adapted instrument used to prepare a cavity of the femur during a minimally invasive hip surgery. For that purpose, the handle assembly is adapted for an anterior approach where the locking pawl that detachably connects to a surgical tool, such as a rasp handle, changes planes from its proximal to distal ends. This provides a relatively short connection to the surgical tool that is optimum in the tight space requirements of a minimally invasive surgery.

These features of the present invention will be apparent upon consideration of the following detailed description in connection with the following drawings.

BRIEF DESCRIPTION OF THE DRAWINGS

FIG. 6 is a side, cross-sectional view of the handle assembly 10 after having been connected to the surgical tool 12.

DETAILED DESCRIPTION OF THE PREFERRED EMBODIMENTS

Figure 1:
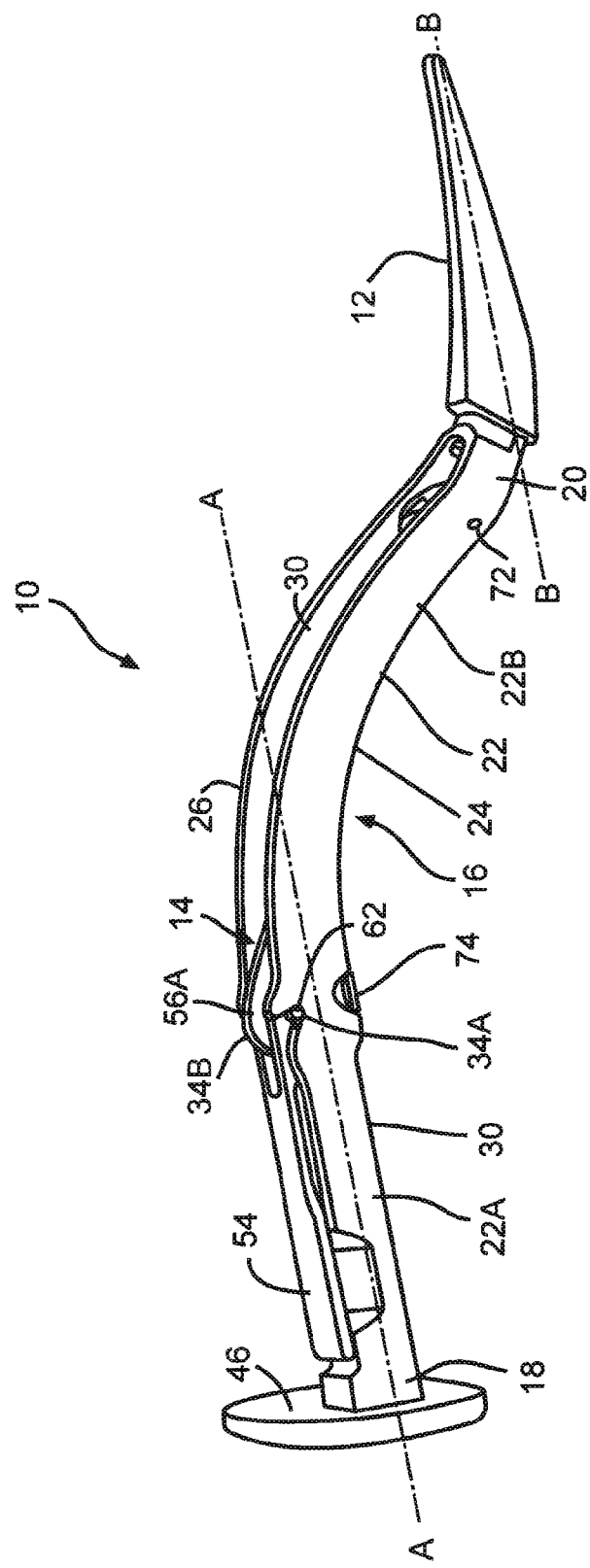
FIG. 1 is a perspective view of a surgical tool handle assembly 10 according to the present invention connected to a surgical tool 12.
Figure 2:
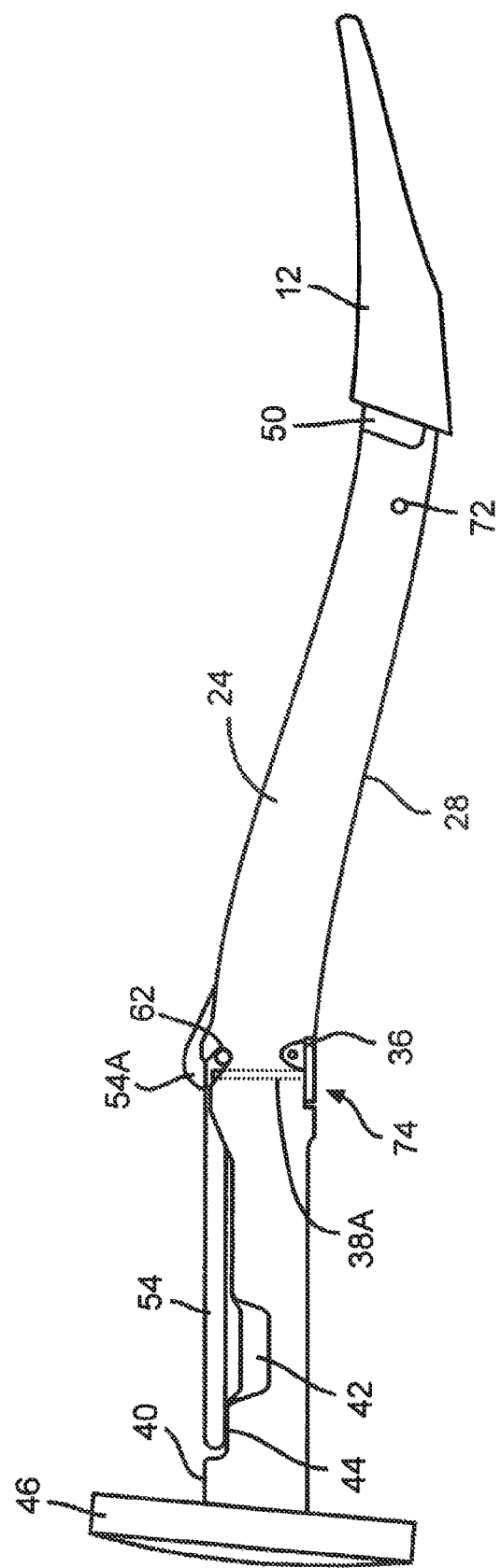
FIG. 2 is a side elevational view of the handle assembly 10 shown in FIG. 1 connected to a surgical tool 12.

Turning now to the drawings, FIGS. 1 to 6 illustrate a surgical tool handle assembly 10 according to the present invention. The handle assembly 10 is shown connected to a surgical broach or rasp 12 for performing a minimally invasive hip replacement surgery. Other tools useful with the handle assembly 10 include, but are not limited to, reamers, angled drivers, twist drills, flexible drills, cannulated drills, bayonet drills, bayonet taps, drill guides, adjustable angle drill guides, taps, and cannulated taps.

The handle assembly 10 generally comprises a linkage train 14 disposed within a housing 16. The housing 16 has a length that extends from a proximal housing section 18 to a distal neck section 20 with an intermediate housing section 22 there between. The intermediate housing section 22 comprises spaced apart right and left side walls 24 and 26 extending upwardly from a bottom wall 28 to an upper opening 30.

A unique feature of the present handle assembly 10 is that the intermediate housing section 22 is further comprised of an axial housing region 22A aligned along the axis A-A and a radiused housing region 22S. As particularly shown in FIG. 3, the radiused housing region 22S provides the side walls 24, 26 with a radiused contour centered about a focal point 32, 32'. The radiused housing region 22B can curve in either a leftward direction or a rightward direction (shown in dashed lines). This construction provides the intermediate section 22 having a linkage chamber with a generally U-shaped cross-section perpendicular to axis A-A and along the curvature of the radiused region 22S extending from the proximal housing section 18. The bottom wall 28 is planar along the proximal housing section 18 and the axial housing region 22A. Further, the intermediate housing section 22 not only curves either to the right or left, depending on the embodiment, but downwardly along the radiused region 22S as well.

A pair of aligned slots 34A, 34S, serving as catch recesses, extends from the upper opening 30 part-way into the height of the respective side walls 24, 26. A recess 36 is provided in the bottom wall 28 vertically below the aligned slots 34A, 34S. A pair of side-by-side vertical bores 38A, 38S (FIG. 3) extends from the recess 36 to the upper edges of the side walls 24, 26 proximally, but adjacent to the respective aligned slots 34A, 34S. The significance of the aligned slots 34A, 34S, the recess 36, and the vertical bores 38A, 38S will be discussed hereinafter.

The intermediate housing section 22 seamlessly meets the proximal housing section 18 having a generally rectangular shape in cross-section perpendicular to the axis A-A provided by the right and left side walls 24, 26, the bottom side wall 28 and an upper side wall 40. The upper side wall 40 is contoured to provide a finger grip region 42 adjacent to a ledge 44. A strike plate 46 is connected to the end of the proximal housing section 18.

Figure 3:
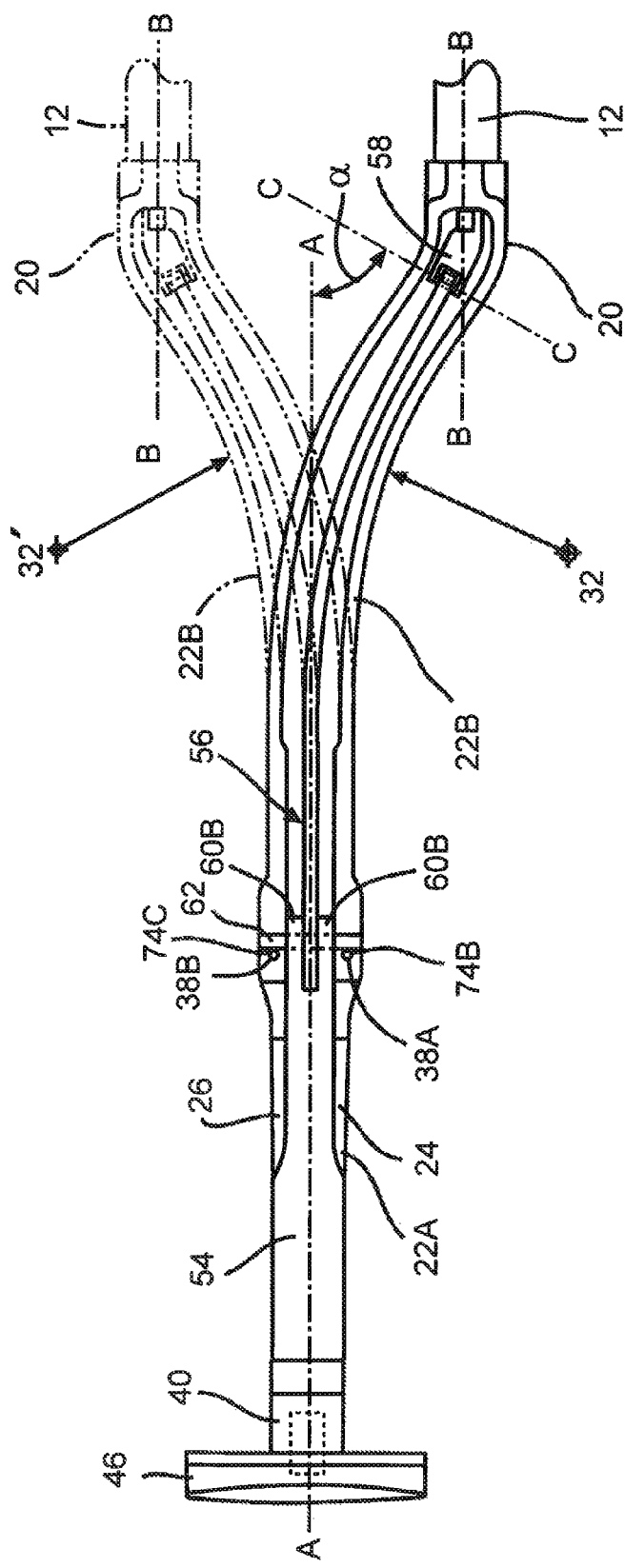
FIG. 3 is a plan view of the handle assembly 10 of FIG. 1 connected to a surgical tool 12 and showing alternate right and left bend embodiments.
Figure 4:
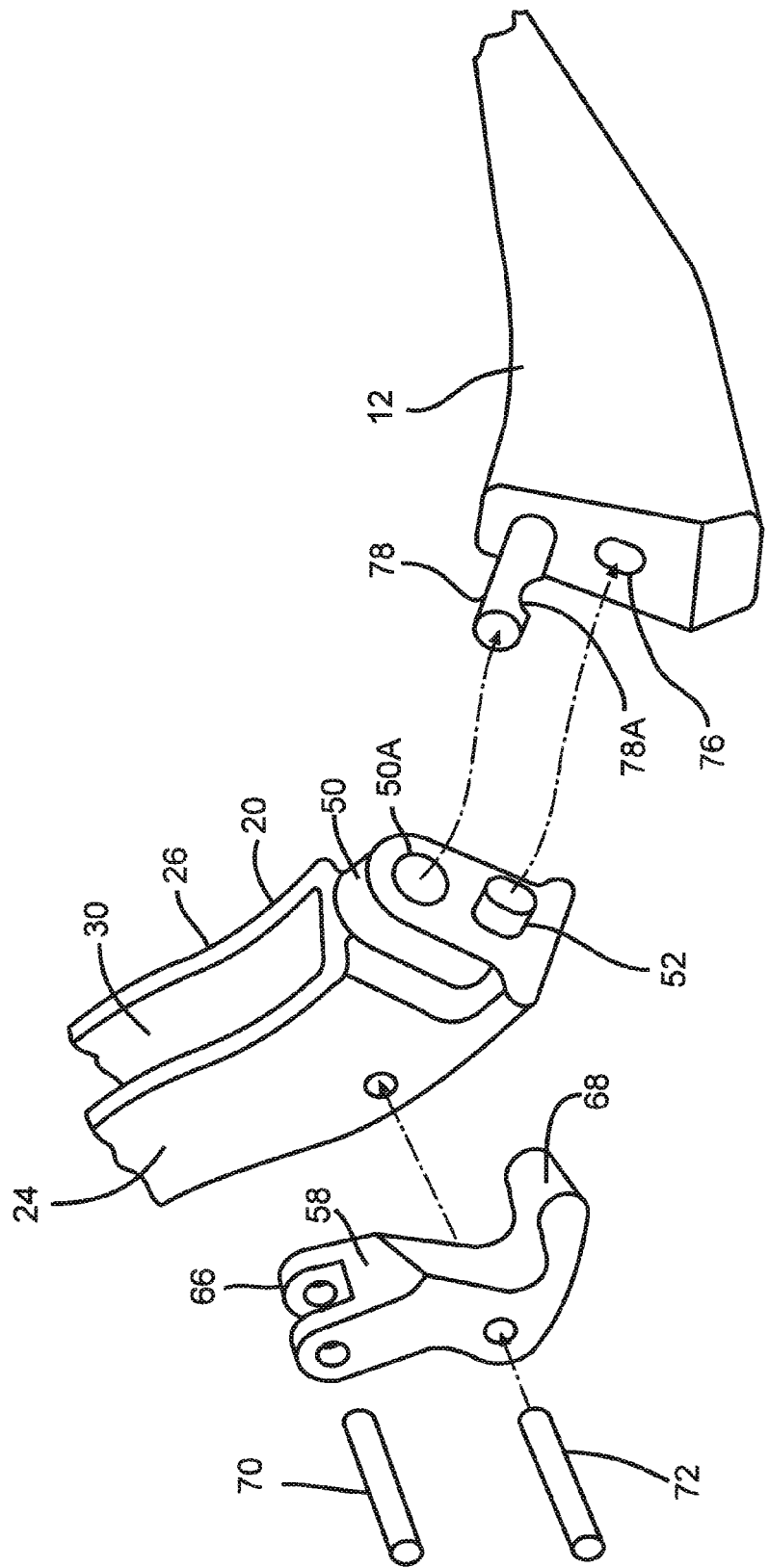
FIG. 4 is a broken-away view of the handle assembly 10 shown in FIG. 1 prior to connection to a surgical tool 12.
Figure 5:
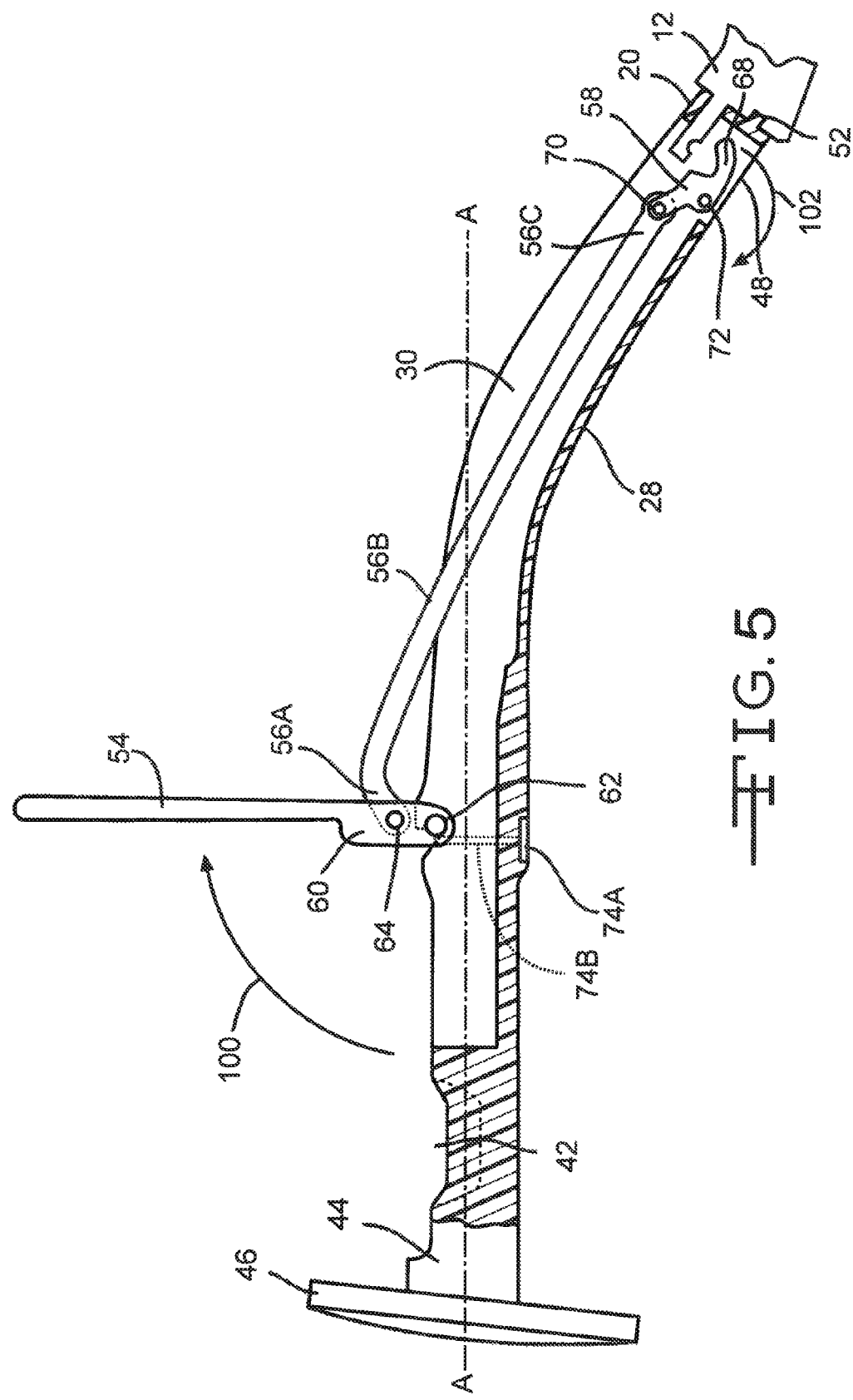
FIG. 5 is a side, cross-sectional view of the handle assembly 10 prior to connection to the surgical tool 12.

The radiused region 22S of the intermediate housing section 22 extends in a downwardly direction until it meets the distal neck section 20 aligned along a second axis B-B (FIGS. 1 and 3). Axis B-B is parallel to, but spaced from, the axis A-A. In that manner, the right and left side walls 24, 26 forming the intermediate housing section 22 seamlessly extend distally and downwardly to form the distal neck section 20 of the housing. However, the bottom wall 28 ends spaced from the distal neck section 20. This provides a distal lower open slot 48 (FIG. 5) that is vertically below that portion of the upper opening 30 residing in the distal neck section 20. At the end of the distal neck section 20, the right and left side walls 22, 26 meet a nose 50 (FIG. 4) supporting a reinforcing extension vertically below a nose opening 50A.

As shown in FIGS. 1 to 4, the linkage train 14 resides inside the housing 16 and comprises a handle lever 54, a main linkage 56 and a locking pawl 58. The handle lever 54 includes a distal head 60 supporting a main fulcrum pin 62 having opposed ends extending outwardly from the handle lever head in an orientation aligned perpendicular to axis A-A. The opposed ends of pin 62 are received in the respective slots 34A, 34B while a proximal end 54A of the handle lever 54 rests on ledge 44. Moving in a proximal direction from the main fulcrum pin 62, the handle lever head 60 divides into spaced apart side walls 60A, 60B providing a gap there between.

The main linkage 56 is an elongate member having a proximal section 56A with its end received in the gap formed by the spaced apart side walls 60A, 60B (FIG. 6) of the handle head 60. The main linkage 56 is pivotably connected to the handle head 60 by a pin 64 located proximally of the fulcrum pin 62 (FIG. 6).

The proximal section 56A of the main linkage 56 is aligned with the axial region 22A of the intermediate housing section 22 along axis A-A. From there, and in a similar manner as the overall contour of the intermediate housing section 22, the main linkage 56 curves into an intermediate radiused portion 56B that coincides with the radiused region 22S of the intermediate housing section until it forms into a distal portion 56C.

The locking pawl 58 is a relatively short member extending from a forked proximal end 66 to an upwardly extending hook 68. The proximal end 66 of the locking pawl 58 is pivotably connected to the distal portion 56C of the main linkage 56 by a second pivot pin 70. Further, a housing pivot pin 72 extends through the locking pawl 58 at an intermediate location between the proximal end 66 and the upwardly extending hook 68. The opposed ends of the housing pivot pin 72 are received in openings in the right and left housing side walls 24, 26 flush with the respective outer surfaces thereof. That way, the hook 68 of the locking pawl 58 is pivotable about a range of motion with respect to the nose opening 50A of the housing 16.

With the linkage train 14 residing inside the right and left side walls 24, 26 and the bottom wall 28 comprising the housing 16, the main linkage 56 extends from the axial housing region 22A of the intermediate housing section 22 at a position adjacent to the proximal housing section 18, along the radiused housing region 22B and to the distal housing neck section 20. The distal neck section 20 is where the main linkage 56 pivotably connects to the locking pawl 58. Importantly, the locking pawl 58 changes planes from its proximal end 66 to distal extending hook end 68. As shown in FIG. 3, the angle α measured between the axis C-C taken along the length of housing pin 72 with respect to axis A-A is from about 30° to about 60°, preferably about 40° to about 50°, more preferably about 45°. This provides a relatively short connection to the surgical tool 12 that is optimum in the tight space requirements of a minimally invasive surgery.

As previously discussed, the proximal portion 56A of the main linkage 54 is pivotably connected to the handle lever 52 at the pivot pin 64, which is proximal of the main fulcrum pin 62 pivotably received in the respective slots 34A, 34S of the right and left side walls 24, 26 of the housing 16.

As particularly shown in FIGS. 2, 3, 5 and 6, a linkage lock mechanism 74 comprises a base plate 74A having a pair of opposed upwardly extending blocking pins 74S, 74O supported thereon. When the linkage train 14 resides in the housing 16 with the main fulcrum pin 62 seated in the slots 34A, 34S, the linkage lock mechanism 74 is moved into position with the blocking pins 74S, 74O residing in the bores 38A, 38S in the respective side walls 24, 26. With the base plate 74A seated in the housing recess 36, the distal ends of the pins 74S, 74O extend upwardly beyond the upper edges of the side walls 24, 26. These extending portions of pins 74S, 74O block the fulcrum pin 62 and, consequently, the linkage train 14 from being removed from inside the housing 16. It should be noted that the pivotable connection between the locking pawl 58 and the distal neck section 20 of the housing 16 at pin 72 prevents the linkage train 14 from being completely separate from the housing.

Because they are supported on side walls comprising the housing, the fulcrum pin 62 and the pivot pin 72 are referred to in the claims as "housing pivot pins". That is regardless whether they are intended to be removable from their supported relationship with the housing, as in the case of fulcrum pin 62, or not, as in the case of pivot pin 72. The other pivot pins 64 and 70 are referred to as "free pivot pins". That is because those latter pivot pins provide for pivotable movement between the various linkage members they connect together without being supported on the housing.

In use, the handle assembly 10 is detachably connectable to a surgical tool 12, such as a broach or rasp, by lifting the handle lever 54 in an upwardly direction (arrow 100, FIG. 5), away from the housing ledge 44. Manipulation is aided by the finger recess 42. As the proximal end of the handle lever 54 moves upwardly, its handle head 60 pivots on the fulcrum pin 62 received in the aligned slots 34A, 34B. This movement, causes the pivot pin 64 to move upwardly and distally to a position essentially vertically aligned directly above the fulcrum pin 62. The main linkage 56, pivotably connected thereto at pin 64, follows along. This causes the distal portion 56C of the main linkage 56 to move both forwardly or proximally and upwardly between the housing side walls 24, 26. In turn, the locking pawl 58 pivots on the housing pivot pin 72 (arrow 102) to move its hook portion 68 from a closely spaced relationship with the housing nose opening 50A to a second position, spaced further away from the nose opening than the first position.

As shown in the drawings, a surgical rasp 12, or similar tool comprising a body designed to wear or cut bone and cartilage by friction, is now mountable onto the handle assembly 10. The surgical tool 12 is provided with an inlet 76 (FIG. 4) and an extension 78 aligned vertically above the inlet. The inlet 76 is sized and configured to receive the housing reinforcing nose 52 in a snug, but slidable fit. The extension 78 is now received in the nose opening 50A with a locking indentation 78A aligned with the hook portion 68 of the locking pawl 58. A locked relationship between the handle assembly 10 and the surgical tool 12 is affected when the handle lever 54 is returned to its original position (arrow 104, FIG. 6), resting against the ledge 44. This return movement causes the lock pawl 58 to pivot, on the housing pivot pin 70 (arrow 106) to move the hook portion 68 back to the closely spaced relationship with the housing nose opening 50A, to thereby reside in the indentation 78A of the surgical tool extension 78. As the locking pawl 58 pivots back to its original position, the main linkage 56 moves proximally. The surgical tool 12 is now firmly locked and secured to the handle assembly 10 for use during a surgical procedure.

As shown in FIG. 6, the drive train 14 is locked into position once the first pivot pin 64 is proximal the fulcrum pivot pin 62 in an "over center" relationship. The over center, locked condition is indicated by arrow 80 as the gap between the two dashed lined centered on pins 62 and 64 with respect to the center of the second pivot pin 70. The surgical tool 12 is now firmly locked and secured to the handle assembly 10 for use during a surgical procedure.

The special relationship between the axial handle region 22A extending along axis A-A and the radiused handle region 22B curving about the focal point 32 (FIG. 3) is a unique feature of the present handle assembly 10. This structure provides a relatively short connection distance from the handle assembly 10 to the surgical tool 12 that is optimum in the tight space requirements of a minimally invasive surgery, such as a hip surgery.

To prepare the handle assembly 10 for cleaning and sterilization, the linkage lock mechanism 74 is manipulated in a direction away from the housing 16 until the blocking pins 74B, 74C are completely removed from the bores 38A, 38B in the respective side walls 24, 26. The linkage train 14 including the handle lever 54 and main linkage 56 is now pivotable out of the housing 16 about housing pivot pin 72. The pivot pin 72 keeps the linkage train 14 from being completely separated from the housing 16. Thus, the linkage train 14 is separable from the housing 16 in a manner that is sufficient to clean and sterilize all of their parts without the possibility of there being total separation of one for the other. Total separation could easily lead to lost and misplaced parts.

The present invention further relates to the handle assembly 10 comprising part of a kit. Typically, a surgical kit comprises a container, the handle assembly 10, and a surgical tool 12 to be connected to the handle assembly. Representative surgical tools 12 include, but are not limited to, broaches, rasps, reamers, angled drivers, twist drills, flexible drills, cannulated drills, bayonet drills, bayonet taps, drill guides, adjustable angle drill guides, taps, and cannulated taps. Instructions for connecting the surgical tool to the handle assembly 10 are also typically provided with the kit.

Additionally, the linkage train 14 and housing 16 are preferably made of a durable material that can be washed and sterilized (e.g., with high heat) to comply with sterilization standards known in the art. In one embodiment, the linkage train 14 and housing 16 are made of metal, such as stainless or a super alloy material. In another embodiment, they are made of a composite material. Though the illustrated embodiment shows the housing 16 as being one piece, in other embodiments it can be modular to facilitate disassembly of the handle assembly 10.

Of course, the foregoing description is that of certain features, aspects and advantages of the present invention, to which various changes and modifications can be made without departing from the spirit and scope of the present invention. Moreover, the handle assembly need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of these specific features and aspects of embodiments may be made and still fall within the scope of the invention.

What is claimed is:

1. A surgical tool handle, which comprises:
  a) a housing providing a linkage chamber extending from a proximal housing section comprising a grip end to a distal housing section comprising a tool end for receiving a tool;
  b) a tool linkage at least partially housed within the linkage chamber, the tool linkage comprising:
    i) a handle lever attached to the housing by a proximal housing pivot pin to thereby provide a first pivotable connection between the tool linkage and the housing;

ii) a locking pawl attached to the housing by a distal housing pivot pin to thereby provide a second pivotable connection between the tool linkage and the housing; and iii) a main linkage comprising a proximal main linkage end connected by a first free pivot pin to the handle lever adjacent to the proximal housing section in a third pivotable connection and a distal main linkage end connected by a second free pivot pin to the locking pawl adjacent to the distal housing section in a fourth pivotable connection; and c) wherein the handle lever is pivotable about the proximal housing pivot pin from a first, opened position spaced a maximum distance along a range of motion from the proximal housing section to a second, closed position spaced at a closer distance along the range of motion relative to the proximal housing section than the first position to thereby cause the main linkage, connected to the handle lever by the first free pivot pin, to move in a proximal direction toward the proximal housing section, to thereby cause the locking pawl, connected to the distal main linkage end by the second free pivot pin, to pivot with respect to the housing on the distal housing pivot pin from an open to a closed position, wherein the open position is configured to either receive a tool for attachment to the housing or release the tool from the housing and wherein the closed position is configured to detachably secure to a tool supported at the distal housing tool end, d) wherein the proximal housing section is aligned along an axis A-A, a radiused housing section extending distally from the proximal housing section curves about a focal point, and the radiused housing section extends distally to the distal housing section aligned along an axis B-B, and e) wherein an angle α measured between an axis C-C taken along the distal housing pivot pin with respect to the axis A-A of the proximal housing section is from about 30° to about 60°.

2. The surgical tool handle of claim 1 wherein the proximal housing pivot pin is supported on the housing in a pair of catch recesses at a position that is distal to the grip end of the proximal housing section, to thereby pivotably mount the handle lever to the housing.

3. The surgical tool handle of claim 2 wherein the proximal housing pivot pin is selectively removable from the pair of catch recesses provided in the housing.

4. The surgical tool handle of claim 1 wherein the distal housing pivot pin is not separable from the housing.

5. The surgical tool handle of claim 1 wherein with the handle lever in the second, closed position, the second pivotable connection between the proximal main linkage end and the handle lever at the first free pivot pin is more proximal than the first pivotable connection of the handle lever and the housing at the proximal housing pivot pin.

6. The surgical tool handle of claim 1 wherein the distal housing pivot pin pivotally supports the tool linkage for pivotable movement out of the linkage chamber for cleaning with the tool linkage remaining connected to the housing at the second pivotable connection of the distal housing pivot pin.

7. The surgical tool handle of claim 1 wherein the tool linkage is removably attached to the housing at the proximal housing pivot pin by a linkage lock mechanism such that when the linkage lock mechanism is in a release position, the tool linkage is pivotable out of the linkage chamber for cleaning with the tool linkage remaining connected to the housing at the second pivotable connection of the distal housing pivot pin.

8. The surgical tool handle of claim 1 wherein a linkage lock mechanism comprises a base plate supporting a pair of side-by-side pins that are received in the housing to block release of the proximal housing pivot pin from removal out of a pair of catch recesses on the housing.

9. The surgical tool handle of claim 1 wherein the radiused housing section curves either in a rightward or a leftward direction with respect to axis A-A of the proximal housing section.

10. The surgical tool handle of claim 1 wherein the angle α with respect to the axis A-A of the proximal housing section is about 45°.

11. The surgical tool handle of claim 1 wherein the housing comprises a bottom wall that is planar along the proximal housing section, but not the radiused housing section.

12. The surgical tool handle of claim 1 wherein the locking pawl is disposed within the distal housing section along the axis B-B parallel to, but spaced from, the axis A-A of the proximal housing section.

13. The surgical tool handle of claim 1 wherein a strike plate is attached to the housing at the grip end of the proximal housing section.

14. The surgical tool handle of claim 1 wherein a reinforcing extension is provided at the distal housing tool end to reinforce a connection between the handle and a surgical tool.

15. The surgical tool handle of claim 1 wherein the locking pawl changes planes from a proximal locking pawl end to a distal extending hook end engageable with a surgical tool.

16. The surgical tool handle of claim 1 wherein the axis A-A of the proximal housing section is parallel to, but spaced from, the axis B-B of the distal housing section.

17. A kit, comprising:
a) a container;
b) a surgical tool handle according to claim 1, wherein the surgical tool handle is disposed within the container; and
c) a tool to be connected to the surgical tool handle, wherein the tool is selected from a group consisting of broaches, rasps, reamers, angled drivers, twist drills, flexible drills, cannulated drills, bayonet drills, bayonet taps, drill guides, adjustable angle drill guides, taps, and cannulated taps.

18. The kit of claim 17 comprising instructions for connecting the tool to the surgical tool handle.

19. A surgical tool handle, which comprises:
a) a housing providing a linkage chamber extending from a proximal housing section comprising a grip end to a distal housing section comprising a tool end for receiving a tool;
b) a tool linkage at least partially housed within the linkage chamber, the tool linkage comprising:
i) a handle lever attached to the housing by a proximal housing pivot pin to thereby provide a first pivotable connection between the tool linkage and the housing;
ii) a locking pawl attached to the housing by a distal housing pivot pin to thereby provide a second pivotable connection between the tool linkage and the housing; and
iii) a main linkage comprising a proximal main linkage end connected by a first free pivot pin to the handle lever adjacent to the proximal housing section in a third pivotable connection and a distal main linkage end connected by a second free pivot pin to the locking pawl adjacent to the distal housing section in a fourth pivotable connection; and c) wherein the handle lever is pivotable about the proximal housing pivot pin from a first, opened position spaced a maximum distance along a range of motion from the proximal housing section to a second, closed position spaced at a closer distance along the range of motion relative to the proximal housing section than the first position to thereby cause the main linkage, connected to the handle lever by the first free pivot pin, to move in a proximal direction toward the proximal housing section, to thereby cause the locking pawl, connected to the distal main linkage end by the second free pivot pin, to pivot with respect to the housing or the distal housing pivot pin from an open to a closed position, wherein the open position is configured to either receive a tool for attachment to the housing or release the tool from the housing and wherein the closed position is configured to detachably secure to a tool supported at the distal housing tool end, d) wherein the proximal housing section is aligned along an axis A-A, a radiused housing section extending distally from the proximal housing section curves about a focal point, and the radiused housing section extends distally to the distal housing section aligned along an axis B-B that is parallel to, but spaced from, the axis A-A of the proximal housing section, and e) wherein an angle $\alpha$ measured between an axis C-C taken along the distal housing pivot pin with respect to the axis A-A of the proximal housing section is from about 30° to about 60°.

\* \* \* \* \*